(12) United States Patent
Marfurt

(10) Patent No.: US 8,416,398 B2
(45) Date of Patent: Apr. 9, 2013

(54) METHOD OF DIFFERENTIATING BETWEEN BLOOD AND CONTROL SOLUTIONS CONTAINING A COMMON ANALYTE

(75) Inventor: Karen L. Marfurt, Edwardsburg, MI (US)

(73) Assignee: Bayer HealthCare, LLC, Tarrytown, NY (US)

( * ) Notice: Subject to any disclaimer, the term of this patent is extended or adjusted under 35 U.S.C. 154(b) by 0 days.

(21) Appl. No.: 13/333,008

(22) Filed: Dec. 21, 2011

(65) Prior Publication Data

US 2012/0149048 A1 Jun. 14, 2012

Related U.S. Application Data

(62) Division of application No. 11/792,194, filed as application No. PCT/US2005/045234 on Dec. 12, 2005, now Pat. No. 8,102, 517.

(60) Provisional application No. 60/635,573, filed on Dec. 13, 2004.

(51) Int. Cl.
*G01N 33/48* (2006.01)

(52) U.S. Cl. .............................. 356/39; 436/44; 422/50

(58) Field of Classification Search ................... 356/39; 436/44; 422/50
See application file for complete search history.

(56) References Cited

U.S. PATENT DOCUMENTS

| | | |
|---|---|---|
| 3,920,580 A | 11/1975 | Mast |
| 4,572,899 A | 2/1986 | Walker et al. |
| 4,729,959 A | 3/1988 | Ryan |
| 4,772,561 A | 9/1988 | Genshaw |
| 4,890,926 A | 1/1990 | Dosmann et al. |
| 5,028,542 A | 7/1991 | Kennamer et al. |
| 5,096,671 A | 3/1992 | Kane et al. |
| 5,120,420 A | 6/1992 | Nankai et al. |
| 5,155,628 A | 10/1992 | Dosmann |
| 5,302,372 A | 4/1994 | Lin et al. |
| 5,321,492 A | 6/1994 | Detwiler et al. |
| 5,361,314 A | 11/1994 | Kopelman et al. |
| 5,429,735 A | 7/1995 | Johnson et al. |
| 5,449,898 A | 9/1995 | Dosmann |
| 5,477,326 A | 12/1995 | Dosmann |
| 5,518,689 A | 5/1996 | Dosmann et al. |
| 5,520,786 A | 5/1996 | Bloczynski et al. |
| 5,605,837 A | 2/1997 | Karimi et al. |
| 5,611,999 A | 3/1997 | Dosmann et al. |

(Continued)

FOREIGN PATENT DOCUMENTS

| | | |
|---|---|---|
| EP | 0555045 | 8/1993 |
| EP | 0 741 186 B1 | 11/1996 |

(Continued)

OTHER PUBLICATIONS

Bettye Hollins et al., "Fluorometric Determination of Indocyanine Green in Plasma" Clinical Chemistry, vol. 33/6, 765-768 (1987).

(Continued)

*Primary Examiner* — Layla Lauchman
(74) *Attorney, Agent, or Firm* — Nixon Peabody LLP

(57) ABSTRACT

Glucose measured in blood samples is distinguished from glucose measured in the control solutions used to test the optical instruments which make such measurements. The control solutions contain a labeling substance recognized by the optical instrument to distinguish glucose measurements made of control solutions from those made of blood samples.

6 Claims, 2 Drawing Sheets

U.S. PATENT DOCUMENTS

| | | | |
|---|---|---|---|
| 5,620,579 A | 4/1997 | Genshaw et al. |
| 5,627,922 A | 5/1997 | Kopelman et al. |
| 5,653,863 A | 8/1997 | Genshaw et al. |
| 5,660,791 A | 8/1997 | Brenneman et al. |
| 5,701,181 A | 12/1997 | Boiarski et al. |
| 5,723,284 A | 3/1998 | Ye |
| 5,798,031 A | 8/1998 | Charlton et al. |
| 5,866,349 A | 2/1999 | Lilja et al. |
| 6,061,128 A | 5/2000 | Zweig et al. |
| 6,157,442 A | 12/2000 | Raskas |
| 6,157,472 A | 12/2000 | Eum et al. |
| 6,181,417 B1 | 1/2001 | Dosmann |
| 6,272,262 B1 | 8/2001 | Kopelman et al. |
| 6,531,040 B2 | 3/2003 | Musho et al. |
| 6,535,753 B1 | 3/2003 | Raskas |
| 6,562,625 B2 | 5/2003 | Modzelewski et al. |
| 6,636,652 B1 | 10/2003 | Kopelman et al. |
| 6,847,451 B2 | 1/2005 | Pugh |
| 7,154,592 B2 | 12/2006 | Reynolds et al. |
| 7,390,665 B2 | 6/2008 | Gilmour et al. |
| 2001/0000129 A1 | 4/2001 | Raskas |
| 2001/0042683 A1 | 11/2001 | Musho et al. |
| 2002/0139692 A1 | 10/2002 | Tokunaga et al. |
| 2003/0149348 A1 | 8/2003 | Raskas |
| 2003/0204182 A1 | 10/2003 | Ahle et al. |
| 2004/0061841 A1 | 4/2004 | Black et al. |
| 2004/0180444 A1 | 9/2004 | Rannikko et al. |
| 2005/0247562 A1 | 11/2005 | Tokunaga et al. |
| 2009/0014339 A1 | 1/2009 | Beer et al. |

FOREIGN PATENT DOCUMENTS

| | | |
|---|---|---|
| EP | 0 762 112 | 3/1997 |
| EP | 1 156 324 A1 | 11/2002 |
| EP | 0 800 086 B1 | 1/2003 |
| JP | 62-157554 | 7/1987 |
| JP | 72-60780 | 10/1995 |
| JP | 2002/306458 | 10/2002 |
| WO | WO 93/21928 A1 | 11/1993 |
| WO | WO 95/13535 A1 | 5/1995 |
| WO | WO 95/13536 A1 | 5/1995 |
| WO | WO 02/087429 | 11/2002 |
| WO | WO 2004/040286 A1 | 5/2004 |
| WO | WO2004/048881 | 6/2004 |
| WO | WO 2005/003622 A1 | 1/2005 |
| WO | WO 2005/040407 A1 | 5/2005 |
| WO | WO 2005/045234 A1 | 5/2005 |
| WO | WO 2005/078118 A1 | 8/2005 |
| WO | WO 2006/110504 A1 | 10/2006 |

OTHER PUBLICATIONS

Hall, J.W. et al., "Automated Determination of Glucose using ENZ Glucose Oxidase and Potassium Ferro Cyanide ENZ Peroxidase," Analytical Biochemistry, vol. 26, No. 1, 1968, pp. 12-17.

Written Opinion of the International Searching Authority corresponding to co-pending International Patent Application No. PCT/US2005/045234, European Patent Office, dated May 2, 2006, 5 pages.

International Search Report corresponding to co-pending International Patent Application No. PCT/US2005/045234, European Patent Office, dated May 2, 2006, 3 pages.

METHOD OF DIFFERENTIATING BETWEEN BLOOD AND CONTROL SOLUTIONS CONTAINING A COMMON ANALYTE

CROSS-REFERENCE TO RELATED APPLICATION

This application is a divisional of U.S. patent application No. 11/792,194 filed Jun. 1, 2007, which is a U.S. national phase of International Application No. PCT/US2005/045234, filed Dec. 12, 2005, which claims the benefit of priority of U.S. Provisional Application No. 60/635,573, filed on Dec. 13, 2004, which are incorporated by reference in their entireties.

BACKGROUND OF THE INVENTION

This invention relates generally to measuring analytes in biological fluids, such as whole blood samples, using optical instruments. Such instruments normally will be tested using solutions that mimic the usual biological sample and contain a known amount of the analyte. The present invention is concerned with identifying a sample as a test solution, commonly called a control solution. More particularly, the invention relates to preventing optical instruments from including in their retained history of measurements those made of the analyte in control solutions. That is, avoiding errors that may occur when the retained history does not accurately report the content of samples previously measured, but includes the results obtained with control solutions.

The quantitative determination of analytes in biological fluids is of great importance in diagnosing and treating medical problems, such as measuring the glucose level in biological fluids, which is important to diabetic individuals. The present invention will be described as it is applied to measuring glucose in blood samples. However, the invention may be applied to other analytes measured in optical instruments.

Both electrochemical and optical methods are used to measure the glucose content of blood. This invention relates to optical measurements. Color changes developed by chemical reactions with the glucose in blood can be measured optically by several types of instruments, including diffuse reflectance, transmittance, absorbance, diffuse transmittance, total transmittance and the like. For example, diffuse reflectance is used in the methods described in U.S. Pat. Nos. 5,611,999 and 6,181,417. Light from light emitting diodes (LEDs) is directed onto a substrate that has been in contact with blood and has developed an optically measurable response. Reflected light is directed to a photodetector where the amount of light received is measured, and correlated with the amount of glucose in the blood sample. In the examples below the absorbance of light was used.

Several types of chemical reactions have been used to cause a change that is detectable by optical instruments. These include reacting glucose with glucose oxidase or glucose dehydrogenase to develop colors which indicate the quantity of glucose in the sample being tested. See for example U.S. Pat. No. 4,689,309. The present invention is not considered to be limited by the type of the chemical reaction used to determine the amount of glucose in blood, provided only that the response to glucose in the sample is detectable by optical instruments.

In order for accurate measurements to be assured, control solutions containing known amounts of glucose are used to verify that the instrument is operating properly. The composition of control solutions has been the subject of a number of patents and publications. Representative are U.S. Pat. Nos. 3,920,580; 4,572,899; 4,729,959; 5,028,542; and 5,605,837; WO 93/21928; WO 95/13535; and WO 95/13536. While control solutions containing blood serum have been used, the more recent patents have been concerned with replacing serum-based control solutions with solutions free of serum, since serum-free solutions are more consistent and stable than those containing serum. The control solution should behave in a manner similar to blood if glucose is to be accurately measured. It will be evident that the composition must be stable over lengthy periods of storage before use. Further, the composition must allow the glucose to react with the reagents that produce color in a manner corresponding to that of glucose contained in a blood sample. Also, the composition should not respond to the light used to illuminate a sample in a way that interferes with the reading of the color developed by reaction of the glucose content with the reagents. Thus, improving the composition of control solutions has been of considerable interest in the art.

Although some control solutions do not add color, others do include colored additives to provide the appearance of blood. For example, U.S. Pat. No. 3,920,580 suggests adding red dye and U.S. Pat. No. 5,605,837 includes a suspension of black particles.

A problem arising in certain instruments relates to the need to distinguish between measurements made with blood samples and those made with control solutions, which are frequently used to assure that the test equipment is performing correctly. If the control solution is formulated to respond in a manner similar to that of a whole blood sample, the instrument does not recognize that a control solution is being tested rather than a blood sample. That is, the glucose content is determined independently of the rest of the sample so that the control solution provides an accurate reading. However, it is common for such instruments to record the glucose measurement and store it, since the history of glucose measurements can be very useful in treating a diabetic patient. Obviously, the glucose content of control solutions should not be included in the recorded history, unless that data can be identified and separated from the glucose measurements of blood samples. Of course, that could be done manually by the user, but through inadvertence the glucose history could be distorted. It would be preferable that the user not be responsible for separating the glucose measurement made of control solutions and blood sample.

In U.S. Pat. No. 5,723,284 electrochemical measurement of glucose in blood is discussed. The '284 patent proposed to modify the control solutions so that the meter would recognize that a control solution was being measured and take appropriate action to prevent the results from being included in the blood sample results. The present invention includes a means for recognizing the presence of a control solution in instruments that measure glucose or other analytes by optical means, as will be described in detail below.

SUMMARY OF THE INVENTION

The invention distinguishes between analytes in biological fluids, particularly glucose in whole or lysed blood, and the analyte in control solutions used to test the performance of an optical instrument. The control solution contains a label, i.e. a substance not found in the normal biological sample, which is recognized by the optical instrument as identifying the control solution. In one example, the optical instrument employs an LED emitting light with a wavelength in the range of from about 600 to about 800 nm corresponding to a characteristic wavelength absorbed by the identifying substance. Preferably, the labeling substance is a dye or a member of the group of water soluble dyes or dyes that can be made water soluble upon addition of surfactants or the like. Typically, the peak absorbance of the dye is within a narrow spectral range that is readily identified as associated with the control solution.

In one aspect, the invention is a method of distinguishing between measurements made of glucose in blood samples and glucose in control solutions. A label substance is added to the control solution, which is recognized by the optical instrument as a control solution, rather than as a blood sample.

In another aspect, the invention is a method of measuring glucose in a blood sample by an optical instrument, wherein a control solution is used to test the performance of the optical instrument, and the control solution contains a substance which serves as a label and which is recognized by the optical instrument as identifying the presence of a control solution.

In a further aspect, the invention is directed to an optical instrument for measuring glucose in whole blood, lysed blood, plasma, or serum by reaction of the glucose with a test strip. The instrument includes a LED-emitting light at a wavelength which characterizes a substance that labels control solutions used to test the performance of the optical instrument. The LED used to detect the labeling substance emits a wavelength absorbed by the label, which is different than the wavelength of the LED used to detect glucose.

In a preferred embodiment, the optical instrument compiles glucose measurements made of whole blood samples, while excluding glucose measurements made of control solutions.

DETAILED DESCRIPTION OF THE PREFERRED EMBODIMENTS

Detection of Glucose by Optical Methods

Figure 1:
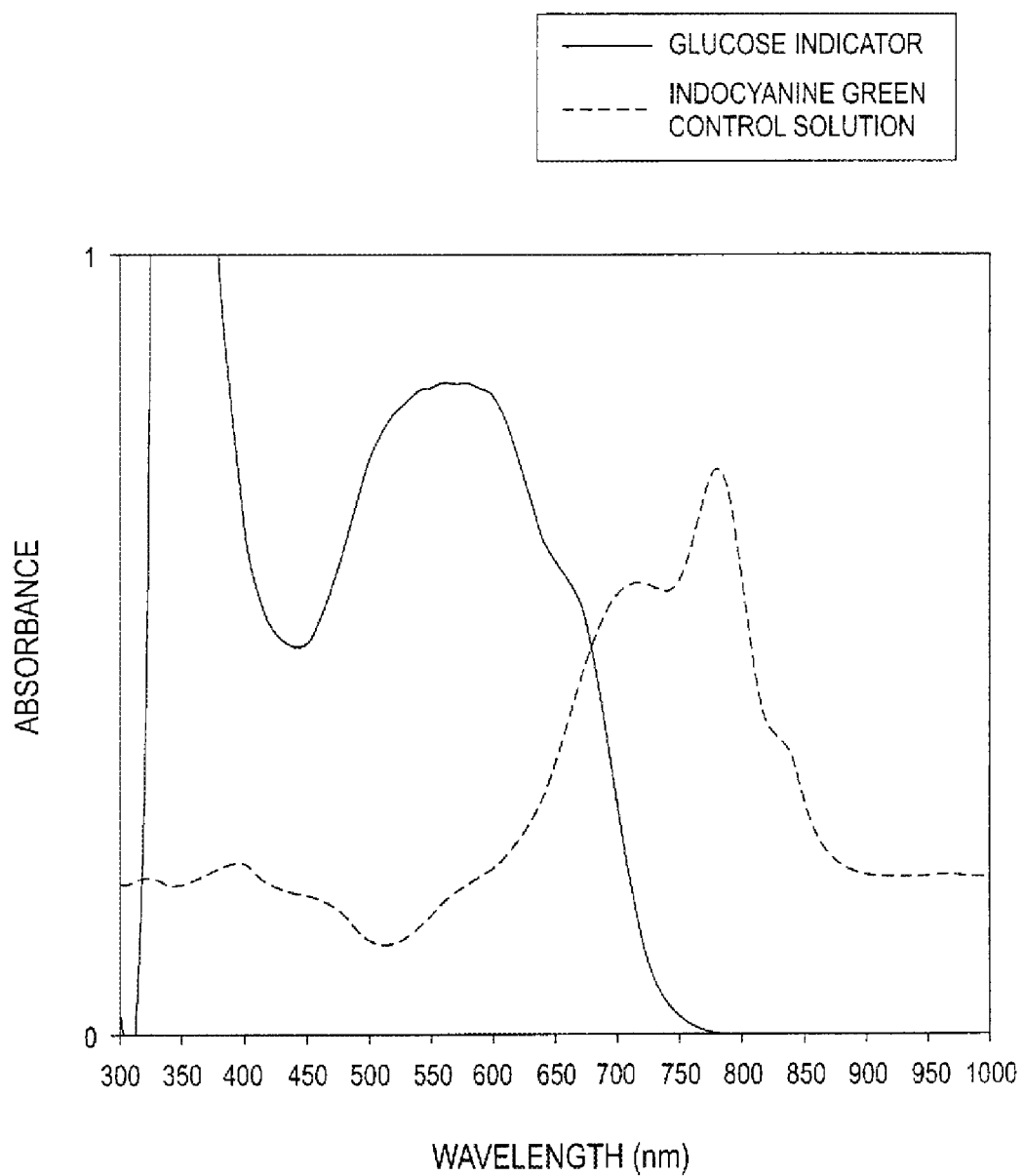
FIG. 1 is an absorbance spectra of the formazan product of WST-4 tetrazolium salt, and of the dye indocyanine green according to one example.

Detection of glucose by optical methods may be broadly divided into those that employ glucose oxidases and those that employ glucose dehydrogenases. Although the methods are similar they use different enzymes, mediators and indicators.

When glucose oxidases are used, the glucose in a sample (e.g., blood) is oxidized to gluconic acid with the release of hydrogen peroxide. The hydrogen peroxide is said to oxidize an indicator (e.g., in the presence of a peroxidase) to produce a measurable optical response (e.g., a color that indicates the amount of glucose in the sample). Some recent patents have suggested that the glucose is converted first to the gluconic acid and then to gluconolactone, while others have suggested that the gluconolactone is formed first and then hydrolyzed to gluconic acid. Regardless of which process sequence is correct, glucose oxidase enzymes have been used widely in dry test strips for measuring the glucose content of blood.

When glucose dehydrogenase enzymes are used, a co-factor is included (e.g., NAD or PQQ), an indicator and a mediator, such as a diaphorase enzyme or an analog thereof. The co-factor is reduced in the presence of the enzyme and the glucose is oxidized to gluconic acid or the gluconolactone as described above. Thereafter, the reduced co-factor is oxidized by the diaphorase or an analog thereof. In this process an indicator, such as a tetrazolium salt, is reduced to produce a colored derivative, which can be measured and correlated with the amount of glucose in the sample being tested.

In the present invention, either of these methods may be employed, since the invention is directed to the use of a control solution by which the performance of the optical instrument is checked to assure that measurements of glucose in whole blood are accurate and reliable.

The methods described above are commonly used in connection with dry test strips containing reagents which react with glucose in a biological sample or a control solution to produce a color, which can be correlated with the amount of glucose present in the sample. While the color developed can provide a semi-quantitative measure of the glucose contained in the sample, for example by comparison of the color with a chart of color versus glucose content, more accurate results are obtained by exposing the colored test strip to a light source, measuring the extent of color development by the indicator used, and correlating the results with the glucose content of the sample.

Control solutions are generally water-based compositions having several basic components that mimic the related biological sample. For measuring glucose in blood, a polymer or polymers is included to provide the solution with the physical characteristics of whole blood. Examples include, but are not limited to, polyethylene oxide, polyhydroxyethyl methacrylate, and polyvinyl pyrrolidone. Typically, the solution comprises from about 5 to about 30% (w/v) polymer. The second component is glucose in a predetermined amount, typically in the range of from about 30 to about 500 mg/dL. A buffer is added to maintain a suitable pH, typically in the range of from about 5 to about 8. Examples include, but are not limited to, citric acid/sodium citrate, phosphoric acid, sodium Hepes, and sodium phosphate. Finally, according to the invention, the solution will contain a labeling substance that produces a characteristic response when exposed to LED light having a wavelength in the range of the peak absorption by the labeling substance. The labeling substance will have a response in a range that is different from that used to determine the glucose content of the control solution. Preferably, the substance used to identify the control solution and to distinguish it from a blood sample will be a dye or a member of the group of water soluble dyes or dyes that can be made water soluble upon addition of surfactants.

In one embodiment, the dye indocyanine green is added to the control solution. As will be seen in the examples below, this dye absorbs light at about 780 nm, making it possible to readily distinguish the presence of the dye and, thus, the presence of control solution.

In the examples below, a dye having a response to light reaching a peak in the 700-820 run region is used to signal that the control solution is being measured. As will be seen, a commonly used indicator for the presence of glucose has a response having a peak in the range of from about 500 to about 650 nm. The separation of the peaks is sufficient to both identify the control solution and to measure the amount of glucose present.

When glucose is measured in whole blood using the optical response of an indicator, the presence of the red blood cells may interfere with the detection of the indicator response. In control solutions, the blood is not present and it is only necessary to assure that the components of the control solution do not interfere with detection of the indicator for the glucose content and the added labeling compound that indicates the presence of a control solution.

EXAMPLE 1

The dye indocyanine green (Sigma Aldrich) was dissolved in a phosphate-buffered saline solution. The absorbance spectra of this solution was measured with a Hewlett-Packard Model 8453 diode-array UV-visible spectrophotometer and the results were plotted in FIG. 1. As shown in FIG. 1, the maximum absorbance was found to be at about 780 nm.

A commercially available tetrazolium salt, WST-4 (Dojindo) was dissolved in 100 millimolar potassium phosphate buffer having a pH of about 7.5. The WST-4 was reduced to the equivalent formazan dye by addition of ascorbic acid, thus simulating the production of a colored indicator in glucose tests. The solution was measured and the results were plotted in FIG. 1 for comparison with the absorbance spectra of the dye indocyanine green. The peak of the absorbance of the formazan was about 550-600 nm, clearly being distinguished from the absorbance of the dye.

EXAMPLE 2

Figure 2:
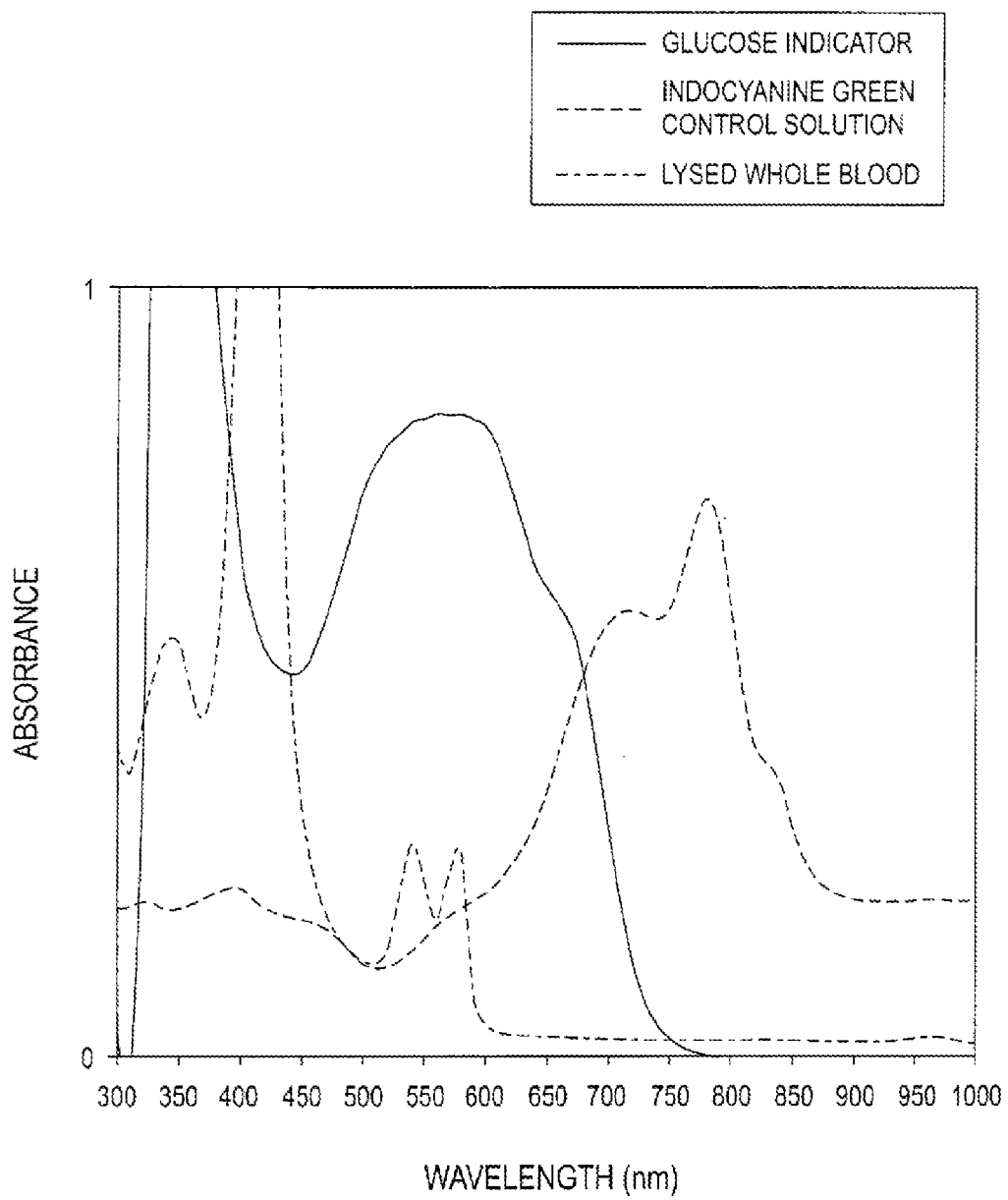
FIG. 2 is an absorbance spectra of lysed whole blood, the formazan product of WST-4 tetrazolium salt, and the dye indocyanine green according to one example.

Whole blood was lysed with a hypotonic solution of water and then diluted in phosphate buffered saline. The absorbance of the lysed blood was measured as in Example 1 and the results plotted in FIG. 2 along with the two absorbance plots of FIG. 1. The maximum absorbance of the lysed blood was about 400 nm, a wavelength clearly distinguished from those of the formazan and indocyanine green. It can be concluded that if blood is lysed as part of a glucose test, that it will not interfere with the labeling dye that indicates the presence of a control solution.

Alternative Embodiment A

A control solution for testing the performance of an optical instrument adapted to measure the concentration of glucose in blood in proportion to the optical response of an indicator, the solution comprising a labeling substance recognized by the optical instrument as identifying the presence of the control solution.

Alternative Embodiment B

The control solution of Alternative Embodiment A wherein the labeling substance has a characteristic response to excitation by a light-emitting diode in the optical instrument that is distinguishable from the response of the indicator.

Alternative Embodiment C

The control solution of Alternative Embodiment A wherein the labeling substance has a peak absorbance of light that is distinguishable from the absorbance of the indicator.

Alternative Embodiment D

The control solution of Alternative Embodiment C wherein the labeling substance is indocyanine green.

Alternative Embodiment E

The control solution of Alternative Embodiment D wherein the labeling substance is distinguished from a tetrazolium salt indicator.

Alternative Process F

A method of distinguishing between measurements in an optical instrument of glucose in blood and glucose in a control solution used to test the performance of the optical instrument, the method comprising the act of adding to the control solution a labeling substance recognized by the optical instrument.

Alternative Process G

The method of Alternative Process F wherein the labeling substance has a characteristic response to excitation by a light-emitting diode in the optical instrument that is distinguishable from the response of the indicator.

Alternative Process H

The method of Alternative Process F wherein the labeling substance has a peak absorbance of light that is distinguishable from the absorbance of the indicator.

Alternative Process I

The method of Alternative Process F wherein the labeling substance is indocyanine green.

Alternative Process J

The method of Alternative Process I wherein the labeling substance is distinguished from a tetrazolium salt indicator.

Alternative Process K

A method of measuring the glucose in blood by an optical instrument, the method comprising the acts of testing the performance of the instrument by adding a control solution containing a known amount of glucose to a test strip adapted to react with the glucose and produce an optical response from an indicator and measuring the response, the control solution contains a labeling substance recognized by the optical instrument and distinguished from the response of the indicator.

Alternative Process L

The method of Alternative Process K wherein the labeling substance has a characteristic response to excitation by a light-emitting diode in the optical instrument that is distinguishable from the response of the indicator.

Alternative Process M

The method of Alternative Process K wherein the labeling substance has a peak absorbance of light that is distinguished from the absorbance of the indicator.

Alternative Process N

The method of Alternative Process M wherein the labeling substance is indocyanine green.

Alternative Process O

The method of Alternative Process N wherein the labeling substance is distinguished from a tetrazolium salt indicator.

Alternative Embodiment P

An optical instrument for correlating the glucose content of blood samples with the optical response obtained by contact of the sample with a test strip adapted to provide the optical response by reaction with the blood sample, the optical instrument comprising a light-emitting diode to excite a response from a labeling substance in a control solution used to distinguish the control solution from the blood samples.

Alternative Embodiment Q

The optical instrument of Alternative Embodiment P wherein the optical instrument compiles glucose measurements and excludes such measurements made of control solutions.

Alternative Embodiment R

The optical instrument of Alternative Embodiment P wherein the labeling substance has a peak absorbance of light distinguished from the peak absorbance of an indicator used to measure the amount of glucose present.

Alternative Embodiment S

The optical instrument of Alternative Embodiment R wherein the substance is indocyanine green.

Alternative Process T

A method of distinguishing control solutions from biological samples in optical instruments used to measure analytes in such biological samples, the method comprising the acts of adding to the control solutions a substance that labels the control solution and enables the optical instruments to identify the control solutions and distinguish the control solutions from the biological samples.

Alternative Process U

The method of Alternative Process T wherein the labeling substance is a dye adapted to being dissolved in the control solution, the dye-absorbing light at a wavelength distinguished from the wavelength of light characterizing the analyte.

While the invention is susceptible to various modifications and alternative forms, specific embodiments are shown by way of example in the drawings and described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

The invention claimed is:

1. A method of measuring the glucose in blood by an optical instrument, the method comprising the acts of testing the performance of the instrument by adding a control solution containing a known amount of glucose to a test strip adapted to react with the glucose and produce an optical response from an indicator and measuring the response, the control solution contains a labeling substance recognized by the optical instrument and distinguished from the response of the indicator, wherein the labeling substance has a peak absorbance of light that is distinguished from the absorbance of the indicator.

2. The method of claim 1, wherein the labeling substance is indocyanine green.

3. The method of claim 2, wherein the labeling substance is distinguished from a tetrazolium salt indicator.

4. The method of claim 1, wherein the labeling substance has a characteristic response to excitation by a light-emitting diode in the optical instrument that is distinguishable from the response of the indicator.

5. The method of claim 1, further comprising compiling the glucose measurements, the glucose measurements excluding control solution measurements.

6. The method of claim 1, wherein the labeling substance is a dye adapted to be dissolved in the control solution.

* * * * *